(12) United States Patent
Shimizu et al.

(10) Patent No.: US 7,820,759 B2
(45) Date of Patent: Oct. 26, 2010

(54) MICELLAR PREPARATION CONTAINING SPARINGLY WATER-SOLUBLE ANTICANCER AGENT AND NOVEL BLOCK COPOLYMER

(75) Inventors: Kazuhisa Shimizu, Maebashi (JP); Toshitaka Murata, Kita-ku (JP); Katsuhiko Sagawa, Namerikawa (JP)

(73) Assignees: Nippon Kayaku Kabushiki Kaisha, Tokyo (JP); Nanocarrier Kabushiki Kaisha, Chiba (JP)

( * ) Notice: Subject to any disclaimer, the term of this patent is extended or adjusted under 35 U.S.C. 154(b) by 0 days.

(21) Appl. No.: 12/322,322

(22) Filed: Jan. 30, 2009

(65) Prior Publication Data

US 2009/0156742 A1 Jun. 18, 2009

Related U.S. Application Data

(62) Division of application No. 10/548,998, filed on Oct. 31, 2005.

(30) Foreign Application Priority Data

Mar. 20, 2003 (JP) .............................. 2003-077607

(51) Int. Cl.
*A61K 47/48* (2006.01)
(52) U.S. Cl. .................................................. 525/54.1
(58) Field of Classification Search ................. 525/54.1
See application file for complete search history.

(56) References Cited

U.S. PATENT DOCUMENTS

| 2001/0014354 A1 | 8/2001 | Yokoyama et al. .......... 424/490 |
| 2005/0119193 A1 | 6/2005 | Motoyama ................... 514/25 |

FOREIGN PATENT DOCUMENTS

| CA | 2 334 615 | 2/2001 |
| CA | 1307866 | 8/2001 |
| CN | 1307866 | 8/2001 |
| EP | 0 583 955 | 2/1994 |
| EP | 1 127 570 | 8/2001 |
| JP | 6-107565 | 4/1994 |
| JP | 6-206815 | 7/1994 |
| JP | 6-206830 | 7/1994 |
| JP | 6-206832 | 7/1994 |
| JP | 8-310970 | 11/1996 |
| JP | 11-335267 | 12/1999 |
| JP | 2001-226294 | 8/2001 |

| WO | 2004/082718 | 9/2004 |

OTHER PUBLICATIONS

English translation of JP 6-206815, 1994.*
The Chinese communication dated Apr. 17, 2009, with English translation.
Chemical Abstracts, American Chemical Society vol. 132, No. 2, Jan. 10, 2000; Nakatomi Ichiro et al. "Polymer Micelle Compositions Containing Poorly Water-Soluble Drugs and Their Preparation" XP002168038.
European communication dated Feb. 17, 2009.
European communication dated Jun. 5, 2009.
The International Search Report dated Nov. 15, 2005 (in co-pending U.S. Appl. No. 11/662,834).
The OA dated Jul. 10, 2009, Apr. 17, 2009 and Jan. 21, 2009 (in co-pending U.S. Appl. No. 10/548,998).
The Office Action dated Mar. 4, 2010 in co-pending U.S. Appl. No. 10/548,998.
Merriam-Webster "Merriam-Webster's Collegiate Dictionary, 11th edition," 2003; Merriam-Websters Inc; entry for "agent,""molecule," and "preparation" pp. 1-22.
English translation of Japanese document JPA-1004-206815, Translation by FLS, Inc. Aug. 2007, pp. 1-24.
International Search Report dated May 11, 2004.
Chinese communication dated Oct. 20, 2006.
Russian communication dated Jun. 27, 2007.

* cited by examiner

*Primary Examiner*—Ling-Siu Choi
*Assistant Examiner*—Sonya Wright
(74) *Attorney, Agent, or Firm*—Nields, Lemack & Frame, LLC

(57) ABSTRACT

A novel micellar preparation in which the solubility of a sparingly water-soluble anticancer agent has been heightened and which after intravenous administration, enables a high blood concentration to be maintained. The preparation has high medicinal activity and/or is reduced in side effects. The micellar preparation is formed from a block copolymer represented by the following general formula (1):

$$R1-(OCH_2CH_2)_n-O-R2-(NHCOCH)_{m-x}-(NHCO-R3-CH)_x-NHR4 \quad (1)$$
$$\phantom{R1-(OCH_2CH_2)_n-O-R2-(NHCOCH)_{m-x}-}|\phantom{(NHCO-R3-CH)_x-}|$$
$$\phantom{R1-(OCH_2CH_2)_n-O-R2-(NHCOCH)_{m-x}-}R3-COR5\phantom{(NH)_x-}COR5$$

[wherein R1 represents hydrogen or $C_{1-5}$ alkyl; R2 represents $C_{1-5}$ alkylene; R3 represents methylene or ethylene; R4 represents hydrogen or $C_{1-4}$ acyl; R5 represents hydroxyl, optionally substituted aryl $C_{2-8}$ alkoxyl, substituted $C_{1-4}$ alkylamino, or amino having a residue of either an amino acid or a peptide derivative; n is an integer of 5 to 1,000; m is an integer of 2 to 300; and x is an integer of 1 to 300; provided that the proportion of hydroxy in the R5's is 0 to 99% and x is not larger than m] and a sparingly water-soluble anticancer agent.

2 Claims, No Drawings

MICELLAR PREPARATION CONTAINING SPARINGLY WATER-SOLUBLE ANTICANCER AGENT AND NOVEL BLOCK COPOLYMER

This application is a divisional of U.S. Ser. No. 10/548,998 filed Oct. 31, 2005, the disclosure of which is incorporated herein by reference.

TECHNICAL FIELD

The present invention relates to a micellar preparation formed from a novel block copolymer and a sparingly water-soluble anticancer agent, an anticancer agent containing the same as an active ingredient, and the block copolymer.

BACKGROUND ART

Many important drugs, particularly anticancer agents, are hydrophobic compounds which are sparingly soluble in water. In order to achieve desired therapeutic effects using such drugs, it is usually required that the drugs be solubilized for administration to patients. Thus, the solubilization of a sparingly water-soluble anticancer agent represents an important technique for making a formulation thereof for oral or parenteral use, particularly for producing a formulation for use in intravenous administration.

One method for solubilizing a sparingly water-soluble anticancer agent is addition of a surfactant. By way of example, a polyoxyethylene castor oil derivative (Cremophor) is used to solubilize paclitaxel. Other methods for solubilizing a sparingly water-soluble anticancer agent include use of a micelle-forming block copolymer as a carrier for the agent, described, for example, in Japanese Patent Application Laying Open (KOKAI) Nos. 6-107565, 6-206815, and 11-335267, and the like, and formation of an included paclitaxel-containing micelle using poly(ethylene oxide)-poly(β-benzylaspartate-co-aspartic acid) block copolymer, described in Japanese Patent Application Laying Open (KOKAI) No. 2001-226294.

However, the solubilization method using a surfactant shows harmful side effects such as hypersensitive reaction due to the surfactant, and also has the problem that, because of low stability of the preparation, agent precipitation occurs when the solution is stored, or allowed to stand for a long period of time.

In addition, intravenous administration of a pharmaceutical preparation using a block copolymer as a carrier for a sparingly water-soluble anticancer agent, e.g. a taxane anticancer agent, has not achieved that it maintains a higher concentration of the agent relative to administration of the agent alone and leads to enhanced pharmacological effects of the agent and reduced side effects thereof.

Thus, there has been a need for a pharmaceutical preparation which enhances the solubility of a sparingly water-soluble anticancer agent in water, which maintains an increased concentration of the agent, and yields enhanced pharmacological effects of the agent and reduced side effects thereof.

Disclosure of the Invention

As the result of intensive studies for solving the above-described problems, the present inventors have discovered a micellar preparation comprising a novel block copolymer and a sparingly water-soluble anticancer agent, thereby accomplishing the present invention.

Thus, the present invention relates to:

1) a micellar preparation formed from a block copolymer represented by general formula (1) below

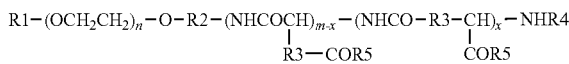

(wherein R1 represents a hydrogen atom or $C_{1-5}$ alkyl group; R2 represents a $C_{1-5}$ alkylene group; R3 represents methylene or ethylene group; R4 represents a hydrogen atom or a $C_{1-4}$ acyl group; R5 represents a hydroxyl group, an optionally substituted aryl $C_{2-8}$ alkoxyl group, a substituted $C_{1-4}$ alkylamino group, or an amino group having a residue of a derivative of an amino acid or a peptide; n is an integer of 5 to 1,000, m is an integer of 2 to 300, and x is an integer of 1 to 300; provided that the proportion of a hydroxyl group in the R5 is 0 to 99% and x is not larger than m) and a sparingly water-soluble anticancer agent;

2) the micellar preparation described in the above 1) wherein the proportion of hydroxyl group in the R5s of general formula (1) is 0% to 90%;

3) the micellar preparation described in the above 1) wherein, in general formula (1), R1 represents a methyl group, R2 represents a trimethylene group, R3 represents a methylene group, R4 represents an acetyl group, and R5 represents an unsubstituted phenyl $C_{3-6}$ alkoxyl group; n is an integer of 20 to 500, m is an integer of 10 to 100, and x is an integer of 1 to 100; provided that x is not larger than m;

4) the micellar preparation described in any one of items 1) to 3) wherein the sparingly water-soluble anticancer agent is a taxane anticancer agent;

5) the micellar preparation described in the above 4) wherein the taxane anticancer agent is paclitaxel;

6) An anticancer agent containing, as active ingredient, the micellar preparation described in any one of items 1) to 5);

7) A block copolymer represented by general formula (1) below

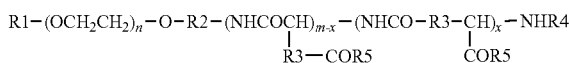

(wherein R1 represents a hydrogen atom or $C_{1-5}$ alkyl group; R2 represents a $C_{1-5}$ alkylene group; R3 represents a methylene or ethylene group; R4 represents a hydrogen atom or a $C_{1-4}$ acyl group; R5 represents a hydroxyl group, an optionally substituted aryl $C_{2-8}$ alkoxyl group, a substituted $C_{1-4}$ alkylamino group, or an amino group having a residue of a derivative of an amino acid or a peptide; n is an integer of 5 to 1,000, m is an integer of 2 to 300, and x is an integer of 1 to 300; provided that the proportion of a hydroxyl group in the R5 is 0 to 99% and x is not larger than m); and 8) the block copolymer described in item 7) wherein, in general formula (1), R1 represents a methyl group, R2 represents a trimethylene group, R3 represents a methylene group, R4 represents an acetyl group, and R5 represents an unsubstituted phenyl $C_{3-6}$ alkoxyl group; n is an integer of 20 to 500, m is an integer of 10 to 100, and x is an integer of 1 to 100; provided that x is not larger than m.

BEST MODE FOR CARRYING OUT THE INVENTION

The micellar preparation of the present invention is formed from a block copolymer represented by general formula (1) above (wherein R1 represents a hydrogen atom or $C_{1-5}$ alkyl group; R2 represents a $C_{1-5}$ alkylene group; R3 represents a methylene or ethylene group; R4 represents a hydrogen atom or a $C_{1-4}$ acyl group; R5 represents a hydroxyl group, an optionally substituted aryl $C_{2-8}$ alkoxyl group, a substituted $C_{1-4}$ alkylamino group, or an amino group having a residue of a derivative of an amino acid or a peptide; n is an integer of 5 to 1,000, m is an integer of 2 to 300, and x is an integer of 1 to 300; provided that the proportion of a hydroxyl group in the R5 is 0 to 99% and x is not larger than m) and a sparingly water-soluble anticancer agent.

In the block copolymer used for the micellar preparation of the invention, R1 is a hydrogen atom or a $C_{1-5}$ alkyl group, preferably a $C_{1-5}$ alkyl group. Specific examples of the $C_{1-5}$ alkyl group include methyl, ethyl, n-propyl, i-propyl, n-butyl, s-butyl, t-butyl, n-pentyl groups, and the like; a methyl group is particularly preferable.

Specific examples of the $C_{1-5}$ alkylene group in R2 include methylene, ethylene, trimethylene, tetramethylene groups, and the like; ethylene and trimethylene groups are preferable.

R3 is a methylene or ethylene group, preferably a methylene group.

R4 is a hydrogen atom or a $C_{1-4}$ acyl group, preferably $C_{1-4}$ acyl groups including formyl, acetyl, propionyl, butyloyl groups, or the like; an acetyl group is particularly preferable.

In the block copolymer used for the micellar preparation of the invention, R5 is a hydroxyl group, an optionally substituted aryl $C_{2-8}$ alkoxyl group, a substituted $C_{1-4}$ alkylamino group, or an amino group having a residue of a derivative of an amino acid or a peptide, and R5s may be the same or different in one molecule. The proportion of hydroxyl group in the R5s is 0% to 99%, preferably 0% to 90%, more preferably 15% to 85%, most preferably 35% to 80%.

The aryl $C_{2-8}$ alkoxyl group may be straight-chain or branched $C_{2-8}$ alkoxyl groups to which an aromatic hydrocarbon group such as a phenyl or naphtyl group is bound, including, for example, a phenethyloxy, phenylpropoxy, phenylbutoxy, phenylpentyloxy, phenylhexyloxy, phenylheptyloxy, phenyloctyloxy, naphthylethoxy, naphthylpropoxy, naphthylbutoxy, or naphtylpentyloxy group.

The substituent in the optionally substituted aryl $C_{2-8}$ alkoxyl group may be lower alkoxyl groups such as methoxy, ethoxy, isopropoxy, n-butoxy, or t-butoxy, halogen atoms such as fluorine, chlorine, or bromine, nitro group, cyano group, or the like. The number of substituents in the optionally substituted aryl $C_{2-8}$ alkoxyl group may be from one to the maximum number for substitution and all substituted aryl $C_{2-8}$ alkoxyl group in which all possible positions are substituted are embraced in the invention; however, the aryl $C_{2-8}$ alkoxyl group is preferably unsubstituted.

The optionally substituted aryl $C_{2-8}$ alkoxyl group may be, preferably unsubstituted phenyl $C_{3-6}$ alkoxyl groups including an unsubstituted phenylpropoxy, unsubstituted phenylbutoxy, unsubstituted phenylpentyloxy, or unsubstituted phenylhexyloxy group; an unsubstituted phenylbutoxy group is particularly preferable.

In R5 of the block copolymer represented by general formula (1) used for the micellar preparation of the invention, the substituted $C_{1-4}$ alkylamino group may be, for example, an optionally substituted aryl $C_{1-4}$ alkylamino group or the like. The aryl $C_{1-4}$ alkylamino group may be straight-chain or branched $C_{1-4}$ alkylamino groups to which an aromatic hydrocarbon group such as a phenyl or naphtyl group is bound, including, for example, a benzylamino, phenethylamino, phenylpropylamino, phenylbutylamino, naphthylmethylamino, naphthylethylamino, or naphthylbutylamino group.

In the optionally substituted aryl $C_{1-4}$ alkylamino group, the substituent may be a lower alkoxyl group such as methoxy, ethoxy, isopropoxy, n-butoxy, or t-butoxy group, a halogen atom suc has fluorine, chlorine, or bromine atom, a nitro group, a cyano group, or the like. The substituted aryl $C_{1-4}$alkylamino group in which the number of substituents is from one to the maximum of substitution and all substituted aryl $C_{1-4}$alkylamino group in which all possible positions are substituted are embraced in the invention; however, the aryl $C_{1-4}$ alkylamino group is preferably unsubstituted.

Particularly preferred examples of the optionally substituted aryl $C_{1-4}$ alkylamino group are unsubstituted benzylamino, unsubstituted phenethylamino groups and the like.

R5 in general formula (1) may be an amino group having a residue of a derivative of an amino acid or a peptide. Such an amino group is a primary amino group comprised in a derivative of an α- or β-amino acid or a peptide in which two or more amino acids are linked through an amide bonding. The derivative of an amino acid or a peptide may be, for example, that having the main chain carboxylic acid esterified, the side chain carboxylic acid esterified, or the side chain hydroxyl group etherified. Specific examples of these include dibenzyl aspartate, β-alanyl-serine benzyl ether benzyl ester (β-alanyl-O-benzyl-L-serine benzyl ester), and the like.

In the block copolymer represented by general formula (1) used for the micellar preparation of the invention, n is an integer of 5 to 1,000, preferably 20 to 500, particularly 80 to 400; m is an integer of 2 to 300, preferably 10 to 100, particularly 15 to 60; x is an integer of 1 to 300, preferably 1 to 100, particularly 1 to 60; provided that x is not larger than m.

A process for preparing the block copolymer represented by general formula (1) is not particularly restricted, but may involve, for example, subjecting a compound in which R5 is an optionally substituted aryl (C2 to C8) alkoxyl or a substituted (C1 to C4) alkylamino group, to partial hydrolysis using acid or alkali, as described in Japanese Patent Application Laying Open (KOKAI) Nos. 11-335267 and 2001-226294.

Of block copolymers represented by general formula (1), a compound having a group other than a hydroxyl group in R5 may be also obtained by the dehydration condensation reaction of a compound of general formula (1) in which R5s are all hydroxyl groups with an optionally substituted aryl $C_{2-8}$ alcohol, a substituted $C_{1-4}$ alkylamine, or a derivative of an amino acid or a peptide. The optionally substituted aryl $C_{2-8}$ alcohol is an alcohol corresponding to the above-described optionally substituted aryl $C_{2-8}$ alkoxyl group. The substituted $C_{1-4}$ alkylamine is an amine corresponding to the above-described substituted $C_{1-4}$ alkylamino group.

As the optionally substituted aryl $C_{2-8}$ alcohol, the substituted $C_{1-4}$ alkylamine, and the derivative of an amino acid or a peptide, commercially available compounds may be used, or compounds prepared by a well-known method for organic synthesis or compounds prepared by applying and combining well-known organic reactions may also be used.

A process for preparing the compound in which R5s are all hydroxyl groups is not particularly restricted, but a method described e.g. in Japanese Patent Application Laying Open (KOKAI) No. 6-206815 may be used.

The dehydration condensation agent used in the above-described dehydration condensation reaction may be, for example, a carbodiimide-based dehydration condensation agent including 1-ethyl-3-(3-dimethylaminopropyl)carbodiimide (EDC), 1-ethyl-3-(3-dimethylaminopropyl)carbodiimide hydrochloride (EDC.HCl), dicyclohexylcarbodiimide (DCC), or diisopropylcarbodiimide (DIPCI).

The dehydration condensation agent is preferably used in an amount of 0.1- to 20-fold moles, particularly 1- to 5-fold moles of the optionally substituted $C_{2-8}$ alcohol, or the substituted $C_{1-4}$ alkylamine. Here, there may also coexist hydroxysuccinimide (HOSu), 1-hydroxybenzotriazole (HOBt), N-hydroxy-5-norbornene-2,3-dicarboxylic acid imide (HOBN), 4-dimethylaminopyridine (DMAP), diisopropylethylamine, or the like in an amount of 0.01- to 20-fold moles, preferably 0.1- to 10-fold moles of the optionally substituted $C_{2-8}$ alcohol, or the substituted $C_{1-4}$ alkylamine.

The amount of the optionally substituted $C_{2-8}$ alcohol, or the substituted $C_{1-4}$ alkylamine used is not particularly restricted, but is preferably 0.1 to 5 equivalents to one equivalent of the carboxyl group of the compound of general formula (1) in which R5s are all hydroxyl.

The dehydration condensation reaction is preferably performed in a solvent; as the solvent various solvents may be used such as, for example, N,N-dimethylformamide (DMF), dimethylsulfoxide (DMSO), dioxane, tetrahydrofuran, water, or a mixture thereof, and is not particularly restricted. The amount of solvent used is not particularly restricted, but is usually 1 to 500 folds based on the weight of a raw material copolymer.

The dehydration condensation reaction is carried out preferably at −10 to 60° C. and could be performed for 2 to 48 hours.

Where the block copolymer represented by general formula (1) used for the micellar preparation of the invention has carboxyl groups, a salt generated by the ionic dissociation of part or all thereof is also embraced in the invention. The salt may be an alkali metal salt, an alkaline earth metal salt, an ammonium salt, or an organic ammonium salt, and for example, specifically including a sodium salt, a potassium salt, a calcium salt, an ammonium salt, or a triethylammonium salt.

The sparingly water-soluble anticancer agent in the micellar preparation of the invention refers to such an anticancer agent as is substantially not dissolved, per se, in the equivalent quantity of water under ambient environment such as room temperature or ordinary pressure, or as is preferentially distributed into a chloroform phase in a solvent system of equal amounts of water and chloroform. Such anticancer agents may include anthracycline anticancer agents such as adriamycin, taxane anticancer agents such as paclitaxel and docetaxel, vinca alkaloid anticancer agents such as vincristine, methotrexate, and derivatives thereof; particularly, a taxane anticancer agent, preferably paclitaxel, is included.

The weight ratio of the block copolymer in the micellar preparation of the invention to the sparingly water-soluble anticancer agent is 1,000:1 to 1:1, preferably 100:1 to 1.5:1, particularly 20:1 to 2:1. However, when the micellar preparation is water-soluble, the agent may be contained in an amount as much as possible.

The micellar preparation of the invention is prepared, for example, by the following methods.

Method a; Inclusion of Agent through Stirring

The sparingly water-soluble anticancer agent, optionally dissolved in a water-miscible organic solvent, is stirred and mixed with a block copolymer aqueous dispersion. In this respect, heating may be carried out during the stirring and mixing.

Method b; Solvent Volatilization

The sparingly water-soluble anticancer agent in a water-immiscible organic solvent is mixed in a block copolymer aqueous dispersion, and the organic solvent is volatilized with stirring.

Method c; Dialysis

The sparingly water-soluble anticancer agent and the block copolymer are dissolved in a water-miscible organic solvent, and the resultant solution is dialyzed against a buffer solution and/or water using a dialysis membrane.

Method d; Other Method

The sparingly water-soluble anticancer agent and the block copolymer are dissolved in a water-immiscible organic solvent. The resultant solution is mixed with water and stirred to form an oil-in-water (O/W) emulsion, followed by volatilizing the organic solvent.

For example, a method for preparing micells in Method c is specifically described e.g. in Japanese Patent Application Laying Open (KOKAI) No. 6-107565.

Methods b and d involving the volatilization of an organic solvent are described, for example, in Japanese Patent Application Laying Open (KOKAI) Nos. 11-335267 and 2001-226294.

More specifically describing Methods b and d, the water-immiscible organic solvent refers to a solvent having the opposite conception to dimethylformamide (DMF), dimethylsulfoxide (DMSO), acetonitrile, and the like which can be substantially freely mixed with water, used for formation of polymer micelles e.g. in Japanese Patent Application Laying Open (KOKAI) No. 11-335267, and is not particularly restricted, but may be chloroform, methylene chloride, toluene, n-hexane, or a mixture thereof.

The water-immiscible organic solvent is mixed with an aqueous medium, i.e. water (including purified water or ion-exchanged water) or an isotonized or buffered aqueous solution containing saccharide, stabilizer, sodium chloride, buffering agent, or the like. Here, a water-miscible organic solvent or other inorganic salt (e.g. sodium sulfate) may be contained in a small amount, to the extent that the formation of the O/W emulsion is not adversely affected.

The water-immiscible organic solvent and the aqueous medium are typically mixed in such a way that the volume ratio is adjusted to 1:100, preferably 1:20. As the mixing means may be used a commonly used means for preparing various emulsions, e.g. a mechanical stirrer, a shaking machine, an ultrasonic irradiator, or the like. In this case, operation temperature is not restricted, but is preferably set to the range of about −5° C. to about 40° C. in consideration of temperature stability of agent, boiling point of solvent, and the like.

Subsequently, the above-described mixing operation is continued in an open system, or the organic solvent is evaporated (or volatilized) for removal under reduced pressure with stirring.

The micellar preparation aqueous solution may be subjected to filtration treatment for insoluble matter or precipitate directly, or after ultrasonication when the micellar preparation is likely to be associated or aggregated. The filtration film used is not restricted, but is preferably a film having a pore size of 0.1 to 1 μm.

The micellar preparation of the invention is stable in aqueous medium, and can provide a higher concentration of the sparingly water-soluble anticancer agent in water compared to the case of not using the additive. In addition, in order to increase the concentration of this agent-containing micellar preparation, enrichment through reduced pressure or ultrafiltration, lyophilization, or the like can be made.

In the micellar preparation, the concentration of agent is 0.1 to 50% by weight, preferably 1 to 40% by weight, particularly 5 to 35% by weight based on the total weight of the agent and the block copolymer; therefore, the amount of the agent may be about 0.01 mg or more, preferably about 1 mg or more, particularly about 2 mg or more for 1 mL of a micellar preparation aqueous solution.

The micellar preparation of the invention may be in the form of a core-shell type micelle in which the structural part of polyethylene glycol is set to the outside in aqueous medium, and includes the sparingly water-soluble anticancer agent in the hydrophobic portion inside the micell. In the case of the core-shell type micelle, the particle size can be measured using a commercially available light scattering particle size measuring device (for example, Otsuka Electronics, Co., Ltd., Model DLS-7000DH); the average particle size is 10 to 200 nm, preferably 20 to 100 nm.

An anticancer agent using, as active ingredient, the above anticancer agent-containing micellar preparation is also embraced in the invention. When the micellar preparation is administered as a pharmaceutical preparation, the dosage thereof is determined depending on the age, weight and pathology of a patient, the therapeutic purpose, and the like; however, the therapeutically effective amount thereof is approximately 50 to 500 mg/body/day. The pharmaceutical preparation administered is not particularly restricted in so far as it has the micellar preparation dissolved in a pharmaceutically acceptable solvent, and may contain pharmacologically acceptable additives. Micellar preparations of the invention also include those lyophilized.

In addition, the present invention encompasses the block copolymer used in the above-described micellar preparation.

EXAMPLES

The present invention is further described, referring to specific preparation examples. However, the invention is not intended to be limited by these examples.

In these examples, ethanol is abbreviated as EtOH; diisopropyl ether as IPE; 4-dimethylaminopyridine as DMAP; N-hydroxysuccinimide as HOSU; and high-performance liquid chromatography as HPLC.

Example 1

Preparing Block Copolymer 6

To 3.56 g of PEG (average molecular weight: 12,000)–pAsp (average degree of polymerization: 35)–Ac (a compound of general formula (1) where R1 represents a methyl group, R2 represents a trimethylene group, R3 represents a methylene group, R4 represents an acetyl group, R5 represents a hydroxyl group; n is about 272, m is about 35, and x is about 26; hereinafter abbreviated as PEG-pAsp-Ac) prepared as described in Japanese Patent Application Laying open (KOKAI) No. 6-206815, was added 70 mL of DMF for dissolving at 35° C., to which DMAP (745 mg), 4-phenyl-1-butanol (1.17 mL), and DIPCI (1.19 mL) were then added, followed by reaction for 26 hours. The reaction liquid was added dropwise to 700 mL of IPE:EtOH (4:1) before filtrating and recovering the precipitate, followed by drying under reduced pressure to provide 3.19 g of a crude crystal. This crude crystal was dissolved in a 50% acetonitrile aqueous solution, which was then passed through 40 mL of a cation exchange resin DOWEX 50w8 (manufactured by Mitsubishi Chemical Corporation), followed by washing with a 50% water-containing acetonitrile. The eluate was vacuum concentrated and then lyophilized to provide 3.85 g of block copolymer 6.

The block copolymer 6 (25.2 mg) was dissolved in 2 mL of acetonitrile, to which 2 mL of 0.5 N sodium hydroxide aqueous solution was added, followed by stirring at room temperature for 20 minutes. After neutralization with 0.5 mL of acetic acid, the fluid volume was adjusted to 5 mL, followed by quantitating free 4-phenyl-1-butanol using HPLC. As the result of analysis, the esterically bonded 4-phenyl-1-butanol was 44% to the polyaspartic acid.

Example 2

Preparing Block Copolymer 7

By a similar operation to that in Example 1, 3.56 g of block copolymer 7 was obtained using 3.59 g of PEG-pAsp-Ac and 0.3 time the amount of 4-phenyl-1-butanol (0.36 mL) as that in Example 1.

As the result of analysis following a similar hydrolysis operation to that in Example 1, the esterically bonded 4-phenyl-1-butanol was 22% to the polyaspartic acid.

Example 3

Preparing Block Copolymer 8

3.02 g of PEG (average molecular weight: 5,000)—pAsp (average degree of polymerization: 30)—Ac (a compound of general formula (1) where R1 represents a methyl group, R2 represents a trimethylene group, R3 represents a methylene group, R4 represents an acetyl group, R5 represents a hydroxyl group; n is about 110, m is about 30, and x is about 22; hereinafter abbreviated as PEG*-pAsp*-Ac) prepared as described in Japanese Patent Application Laying Open (KOKAI) No. 6-206815, was used to perform condensation reaction with 4-phenyl-1-butanol (1.45 mL) by a similar operation to that in Example 1 to provide 3.05 g of block copolymer 8.

As the result of analysis following a similar hydrolysis operation to that in Example 1, the esterically bonded 4-phenyl-1-butanol was 50% to the polyaspartic acid.

Example 4

Preparing Block Copolymer 9

By a similar operation to that in Example 1, 2.74 g of block copolymer 9 was obtained using 3.04 g of PEG*-pAsp*-Ac and 0.3 time the amount of 4-phenyl-1-butanol (0.44 mL) as that in Example 3.

As the result of analysis following a similar hydrolysis operation to that in Example 1, the esterically bonded 4-phenyl-1-butanol was 25% to the polyaspartic acid.

Example 5

Preparing Block Copolymer 10

By a similar operation to that in Example 1, 233 mg of block copolymer 10 was obtained using 200 mg of PEG-pAsp-Ac, and 6-phenyl-1-hexanol (80.1 μL) instead of 4-phenyl-1-butanol used in Example 1.

As the result of analysis following a similar hydrolysis operation to that in Example 1, the esterically bonded 6-phenyl-1-hexanol was 48% to the polyaspartic acid.

Example 6

Preparing Block Copolymer 13

In 4 mL of DMF was dissolved 200 mg of PEG-pAsp-Ac, to which 49.8 mg of HOSu, 23.6 µL of benzylamine, and 74.6 µL of DIPCI were then added, followed by reaction at 35° C. for 4 hours. To the reaction liquid was added 100 µL of distilled water before stirring for 15 minutes, to which 60 mL of IPE:EtOH (9:1) was then added dropwise before filtrating and recovering the precipitate, followed by drying under reduced pressure to provide 189 mg of block copolymer 13.

The benzylamine remaining in the reaction liquid was quantitated; as the result of calculation based on that, the amidically bonded benzylamine was 61% to the polyaspartic acid.

Example 7

Preparing Block Copolymer 15

By a similar operation to that in Example 6, 3.35 g of block copolymer 15 was obtained using dibenzyl L-aspartate toluenesulfonate (715 mg) and diisopropylethylamine (257 µL) instead of benzylamine used in Example 6, and 3.09 g of PEG-pAsp-Ac.

By hydrolysis in similar conditions to those in Example 1, free benzylalcohol was quantitated for analysis; dibenzyl L-aspartate amidically bonded to block copolymer 15 was 23% to the polyaspartic acid.

Example 8

Preparing Block Copolymer 16

By a similar operation to that in Example 6, 1.49 g of block copolymer 16 was obtained using β-alanyl-O-benzyl-L-serine benzyl ester hydrochloride (321 mg) preparable by a conventional dipeptide synthesis method and diisopropylethylamine (142 µL) instead of benzylamine used in Example 6, and PEG-pAsp-Ac (1.51 g).

As the result of analysis using a similar method to that in Example 7, β-alanyl-O-benzyl-L-serine benzyl ester amidically bonded to block copolymer 16 was 26% to the polyaspartic acid.

Example 9

Preparing Paclitaxel Micellar Preparation 10

300 mg of block copolymer 6 in Example 1 (a block copolymer with 4-phenyl-1-butanol condensed) was weighed into a screw tube bottle, to which 30 mL of a 40 mg/mL maltose aqueous solution was then added before stirring to form a dispersion, followed by cooling to 4° C. with stirring. Further, 3 mL of a dichloromethane solution of paclitaxel (30 mg/mL) was added before stirring without sealing hermetically in a refrigerator for 16 hours, followed by ultrasonication (130 W, 1 secPulse, for 10 minutes). Macrogol 4,000 was added to a concentration of 20 mg/mL for dissolution, followed by filtrating in sterile condition to provide micellar preparation 10.

The concentration of paclitaxel was 2.8 mg/mL. The average particle size was 86.6 nm as determined by a dynamic light scattering photometer (Otsuka Electronics, Co., Ltd., Model DLS-7000DH).

Similarly, the block copolymers described in Examples were used to produce paclitaxel micellar preparations. The results obtained are shown in Table 1.

TABLE 1

| Micellar preparations | | | |
|---|---|---|---|
| Micellar preparation | Block copolymer | Agent concentration (mg/mL) | Particle size (nm) |
| 10 | 6 | 2.8 | 86.6 |
| 11 | 7 | 3.1 | 97.8 |
| 12 | 8 | 2.8 | 53.3 |
| 13 | 9 | 3.0 | 85.3 |
| 18 | 15 | 2.0 | 85.1 |
| 19 | 15 | 4.5 | 20.1 |
| 20 | 16 | 2.0 | 28.8 |

Comparative Example

In accordance with Japanese Patent Application Laying Open (KOKAI) No. 6-107565, 10 g of a polyethylene glycol derivative having a methoxy group on one terminal and an amino group on another terminal and commercially available β-benzyl L-aspartate N-carboxylic anhydride were dissolved in 80 mL of the mixed solvent of DMF/DMSO (50%/50%) for reaction at 40° C. for 24 hours with shielding the light using aluminum foil. Subsequently, the reaction solution was added dropwise to 660 mL of the mixed solvent of n-hexane/ethyl acetate (50%/50%) to reprecipitate the polymer. Three rounds of the reprecipitation operation were conducted, followed by drying under reduced pressure for 24 hours to provide about 19 g of poly(ethylene oxide; average molecular weight:12,000)-poly(β-benzyl aspartate; average degree of polymerization: 50) block copolymer.

In 100 mL of acetonitrile was dissolved 10 g of the resultant block copolymer, to which 22.72 mL of a 0.5 N sodium hydroxide aqueous solution was then added for hydrolysis reaction at room temperature for 10 minutes, The reaction was terminated by adding 3.79 mL of 6 N hydrochloric acid, followed by transferring the reaction liquid to a dialysis membrane (Spectra/Por7, MWCO 3,500) to perform dialysis against 3.3 L of ion exchanged water for 9 hours or more (the ion exchanged water was replaced three times or more). After the end of dialysis, filtration was carried out using a filter paper No. 5B (Kiriyama Glass Works Co., 4 µm), followed by lyophilization to provide about 9 g of poly(ethylene oxide)-poly(β-benzyl aspartate-co-aspartic acid) block copolymer, about 50% of which was hydrolyzed.

300 mg of the resultant block copolymer was weighed into a screw tube bottle, to which 30 mL of a 40 mg/mL maltose aqueous solution was added before stirring to make a dispersion, followed by cooling to 4° C. with further stirring. 3 mL of a dichloromethane solution of paclitaxel (20 mg/mL) was added before stirring without sealing hermetically in a refrigerator for 16 hours, followed by ultrasonication (130 W, 1 secPulse, for 10 minutes).

Part of the sample was taken and subjected to particle size determination using a dynamic light scattering photometer (Otsuka Electronics, Co., Ltd., Model DLS-7000DH). The average particle size was 107 nm.

Subsequently, Macrogol 4,000 was added to a concentration of 20 mg/mL for dissolution before filtrating in sterile condition, followed by lyophilization to provide a micellar preparation for Comparative Example.

Test Example 1

In Vivo Antitumor Effect against Colon 26

Female CDF1 mice were inoculated subcutaneously at the back thereof with the mouse colon cancer Colon 26 cells, and, from the point of time when the volume of tumor has reached around 100 mm$^3$, micellar preparation 10 according to the invention, the micellar composition from Comparative Example, or paclitaxel was administered through the tail veins of the mice for consecutive 5 days to examine effects against advanced cancer. Each agent was used directly, or after dilution with saline before use. The concentration of each agent was expressed in terms of paclitaxel. The antitumor effect of agent was judged on the basis of a percentage of the average tumor volume in treated group to the average tumor volume in untreated group (T/C %) 11 days after agent treatment. The results obtained are shown in Table 2.

TABLE 2

Antitumor effects against the mouse colon cancer Colon 26

| Administered agent | Dose (mg/kg) | T/C (%) |
|---|---|---|
| Micellar preparation 10 | 30 | 13.4 |
| Micellar preparation from Comparative Example | 30 | 42.2 |
| Paclitaxel | 30 | 37.5 |
| Paclitaxel | 30 | 40.0 |

As shown in Table 2, paclitaxel alone exhibited tumor shrinkage rates of 37.5% or 40.0% in the 30 mg/kg treated group as compared to untreated group 11 days after treatment; the benzyl ester-type micellar preparation from Comparative Example exhibited the rate of 42.2%, showing almost the same effect as paclitaxel alone; however, micellar preparation 10 according to the invention exhibited the rate as low as 13.4%, showing a significantly higher antitumor effect.

Test Example 2

Transition of Paclitaxel Concentrations in the Rat Plasma

Micellar preparation 10 from Example 9 was diluted with normal saline solution to make an aqueous solution having a concentration of 2.5 mg/mL in terms of paclitaxel. Paclitaxel alone was dissolved in ethanol, to which Cremophor (Sigma) was then added in the same amount as ethanol to prepare in such a way that the concentration of paclitaxel was adjusted to 25 mg/mL, followed by dilution to 2.5 mg/mL with normal saline solution immediately before administration. Micellar preparation 10 or paclitaxel alone was administered in an amount equivalent to paclitaxel 5 mg/kg to male SD rats through their tail veins, followed by taking blood samples from their cervical veins with time. The plasma obtained by centrifugation was diluted with an appropriate amount of water and subjected to three rounds of extraction with t-butyl methyl ether. The ether layer was recovered, dried up, and then dissolved in 50 μL of actonitrile, followed by quantitating paclitaxel using HPLC. The results obtained are shown in Table 3.

TABLE 3

Paclitaxel concentrations (μg/mL) in the rat plasma

| Blood drawing time (min.) | Micellar preparation 10 | Paclitaxel |
|---|---|---|
| 10 | 66.01 | 1.05 |
| 30 | 53.68 | 0.51 |
| 60 | 38.27 | 0.26 |
| 120 | 30.02 | 0.10 |
| 360 | 7.07 | 0.035 |
| AUC (0-360) (min · μg/mL) | 10236 | 70.42 |

As indicated in Table 3, the administration of the micellar preparation of the invention leaded to the maintenance of higher plasma concentrations of paclitaxel than that of paclitaxel alone. In the area under the blood concentration-time curve (AUC), paclitaxel alone: micellar preparation of the invention was 1: about 150.

Test Example 3

Toxicity Test against Mouse Extension Reflex (Peripheral Nerve Impairment)

Micellar preparation 10 or paclitaxel alone was administered to female CDF1 mice through their tail veins for consecutive 5 days to observe the extension reflex of their hind limbs providing an indication of peripheral nerve impairment due to paclitaxel. Each agent was prepared as described in Test Example 1, and used directly, or after dilution with saline before use. The dosages used were expressed in terms of paclitaxel. The results obtained are shown in Table 4.

TABLE 4

Toxicity against mouse extension reflex (Peripheral nerve toxicity)

| Administered agent | Dose (mg/kg) | Mice showing extension reflex disappearance |
|---|---|---|
| Micellar preparation 10 | 30 | 0/3 |
| Paclitaxel | 30 | 3/3 |

As indicated in Table 4, paclitaxel alone induced the disappearance of extension reflex in all mice of the 30 mg/kg treatment group. In contrast, micellar preparation 10 produced no disappearance of extension reflex in the 30 mg/kg treatment group. The micellar preparation of the invention reduced peripheral nerve toxicity as a side effect of paclitaxel, compared to paclitaxel alone.

Advantage of the Invention

The micellar preparation of the invention enables a necessary amount of agent, particularly paclitaxel, to be entrapped in micells without binding to a macromolecule, and, when administered, leads to the maintenance of increased blood concentrations of paclitaxel compared to those for paclitaxel alone. As a result, the preparation may have an enhanced medicinal activity compared to paclitaxel alone, and may also reduce the toxicity observed in paclitaxel alone, enabling a useful pharmaceutical preparation to be provided. In addition, an anticancer agent containing the micellar preparation as active ingredient is also provided.

Further, a block copolymer suitable for forming the micellar preparation with the above-described effect is also provided. Use of the block copolymer has enabled the solubility of a sparingly water-soluble anticancer agent in water to be heightened.

In addition, an aqueous solution of the micellar preparation of the invention produces, when left at rest at room temperature, no association of micells or release of agent from the micellar preparation for at least several hours, enabling the provision, by the invention, of a micellar preparation containing a sparingly water-soluble anticancer agent, retained stably in aqueous medium.

The invention claimed is:

1. A block copolymer represented by general formula (1) below

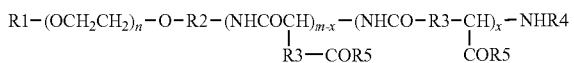
(1)

wherein R1 represents a hydrogen atom or $C_{1-5}$ alkyl group; R2 represents a $C_{1-5}$ alkylene group; R3 represents a methylene or ethylene group; R4 represents a hydrogen atom or a $C_{1-4}$ acyl group; R5 represents a hydroxyl group, an optionally substituted aryl $C_{2-8}$ alkoxyl group, or an amino group having a residue of a derivative of an amino acid or a peptide; n is an integer of 5 to 1,000, m is an integer of 2 to 300, and x is an integer of 1 to 300; provided that the proportion of a hydroxyl group in the R5 is 0 to 99% and x is not larger than m.

2. The block copolymer according to claim 1, wherein, in general formula (1), R1 represents a methyl group, R2 represents a trimethylene group, R3 represents a methylene group, R4 represents an acetyl group, and R5 represents an unsubstituted phenyl $C_{3-6}$ alkoxyl group; n is an integer of 20 to 500, m is an integer of 10 to 100, and x is an integer of 1 to 100; provided that x is not larger than m.

* * * * *